(12) United States Patent
Jain et al.

(10) Patent No.: US 8,390,047 B2
(45) Date of Patent: Mar. 5, 2013

(54) MINIATURIZED IMPLANTABLE SENSOR PLATFORM HAVING MULTIPLE DEVICES AND SUB-CHIPS

(76) Inventors: Faquir Chand Jain, Storrs, CT (US); Fotios Papadimitrakopoulos, West Hartford, CT (US)

( * ) Notice: Subject to any disclaimer, the term of this patent is extended or adjusted under 35 U.S.C. 154(b) by 540 days.

(21) Appl. No.: 12/590,883

(22) Filed: Nov. 16, 2009

(65) Prior Publication Data
US 2010/0148293 A1 Jun. 17, 2010

Related U.S. Application Data

(60) Provisional application No. 61/114,731, filed on Nov. 14, 2008.

(51) Int. Cl.
*A61B 5/00* (2006.01)
(52) U.S. Cl. ........ 257/309; 257/431; 257/432; 257/433; 257/434
(58) Field of Classification Search .......... 257/431–434; 600/309
See application file for complete search history.

(56) References Cited

U.S. PATENT DOCUMENTS

| 5,625,209 A * | 4/1997 | Appleton et al. ............. 257/253 |
| 7,581,443 B2 * | 9/2009 | Kubena et al. ............. 73/504.12 |
| 2008/0154101 A1 * | 6/2008 | Jain et al. ............... 600/309 |

* cited by examiner

*Primary Examiner* — David Vu
*Assistant Examiner* — Brandon Fox
(74) *Attorney, Agent, or Firm* — Steven M. McHugh

(57) ABSTRACT

An implantable, miniaturized platform and a method for fabricating the platform is provided, where the e platform includes a top cover plate and a bottom substrate, top cover plate including an epitaxial, Si-encased substrate and is configured to include monolithically grown devices and device contact pads, the Si-encased substrate cover plate including a gold perimeter fence deposited on its Si covered outer rim and wherein the bottom substrate is constructed of Si and includes a plurality of partial-Si-vias (PSVs), electronic integrated circuits, device pads, pad interconnects and a gold perimeter fence, wherein the device pads are aligned with a respective device contact pad on the top cover plate and includes gold bumps having a predetermined height, the top cover plate and the bottom substrate being flip-chip bonded to provide a perimeter seal and to ensure electrical connectivity between the plurality of internal devices and at least one external component.

38 Claims, 11 Drawing Sheets

MINIATURIZED IMPLANTABLE SENSOR PLATFORM HAVING MULTIPLE DEVICES AND SUB-CHIPS

CROSS REFERENCE TO RELATED APPLICATIONS

This application claims the benefit of U.S. Provisional Patent Application No. 61/114,731, filed Nov. 14, 2008 and entitled "Integration and Passivation Methodologies for Miniaturized Implantable Sensor Platform Consisting of Multiple Devices and Sub-chips" the contents of which are incorporated herein by reference in its entirety.

FIELD OF THE INVENTION

This invention relates generally to a biosensor platform and more particularly to an integrated, implantable, biosensor platform, which is sealed to permit long-term operation within a physical body.

BACKGROUND OF THE INVENTION

Implantable biosensor platforms are complex miniaturized devices that are geared to monitor the concentration of metabolites and other biochemicals in their immediate vicinity. One example of such a biosensor device is an implantable glucose sensor that can assist in the proper management of diseases, such as diabetes mellitus. In general, such biosensor platforms consist of many components in addition to the actual biosensing element. Such components typically include electronic, optoelectronic, micro-electromechanical (MEM), ultrasound and radiofrequency (RF) devices, which are configured for powering, signal processing and wireless communication operations. In the presence of moisture and oxygen, these components are particularly sensitive to corrosion and therefore should be packaged in such a way that they are impervious to their environmental elements, such as gases and body fluids. On the other hand, current electrochemical sensing element (or elements) must be in direct contact with biological fluids in order to establish operable functionality. However, in the case of extreme miniaturization, such dual environmental requirements present major fabrication issues. To complicate matters, a variety of temperature and environmentally-sensitive biomolecules should be properly deposited on these sensors and coated with a number of semipermeable membranes and/or drug containing entities to help regulate analyte diffusion, provide biocompatibility, suppress inflammation and prevent fibrosis.

Current device packaging can be divided into two parts: (A) sub-chip assembly and (B) device passivation. In terms of sub-chip assembly, chip to chip interconnects are typically formed using: (i) through-Si-vias (TSVs), (ii) flip-chip thermo-compression and thermosonic bonding, and (iii) wire bonding in either flat or wrap-around configurations. In terms of device passivation, techniques like (i) polymer encapsulation, (ii) thermo-compression molding, and (iii) sputtering or chemical vapor deposition (CVD) growth of a variety of insulating organic and inorganic materials have been employed. Unfortunately, these techniques fail to attain the required passivation needed for devices with the aforementioned dual environmental requirements, particularly when they reach extreme miniaturization and prolonged exposure to body fluids.

For example, referring to FIG. 1 a schematic block diagram of an IC chip 300 having device packaging in accordance with the prior art is illustrated and shows a variety of interconnects along with a through-Si-via (TSV) and flip-chip bonding of two individual IC wafers. In this case, two Si wafers (1) and (2) with their respective devices (3) and (4) are shown as being electrically connected via their interconnects (6) and (8), respectively, where the electrical connection is achieved through flip-chip bonding via a bonding layer (12). The interconnects (6) and (8) are shown as being isolated by host oxide layers (5). A TSV (10), which is isolated from the top wafer (2) by insulators (7) and (9), electrically connects the back side metal layer (11) to the top wafer interconnect layer (8). Such a conventional through-Si-via (TSV) requires the formation of a hole through the entire top wafer. This is undesirable because such holes, despite their metal filling, make this packaging prone to a variety of leakages should this wafer be exposed to a corrosive environment.

SUMMARY OF THE INVENTION

A device platform is provided and includes at least one internal component, wherein the device platform is configured to isolate the at least one internal component from an environment external to the device platform while providing for electrical connectivity to at least one external component externally located on the outer surface of the device platform. The device platform also includes an enclosure, the enclosure including a top cover plate and a bottom substrate configured to define a sealed enclosure cavity for containing the at least one component, wherein the top cover plate is configured to allow reception and transmission of electromagnetic radiation, the surface of the top cover plate adjacent the enclosure cavity being covered with an epitaxial Si film in intimate cohesion, and wherein the bottom substrate is constructed of a high resistivity Si having a Si substrate material conductivity and includes at least one partial Si via (PSV), wherein the at least one partial Si via (PSV) is configured to electrically connect the at least one internal component with the at least one external component, and wherein the partial Si via (PSV) is formed by introducing a dopant with the Si material, wherein the combination of the dopant and the Si material results in at least one of a reduced conductivity and a conductivity that is opposite to that of the Si substrate material conductivity, and wherein an outer perimeter of each of the surface of the top cover plate adjacent the enclosure cavity and a surface of the bottom substrate adjacent the enclosure cavity includes a continuous gold fence cohesively bonded to its respective Si surface, wherein the top cover plate and the bottom substrate are configured such that the enclosure cavity is sealed using a gold-to-gold bond.

A method for integrating a plurality of device into a device platform is provided and includes forming the device platform using a top cover plate and a bottom substrate separated by at least one Si spacer, wherein the device platform defines a device cavity and the top cover plate is configured to allow electromagnetic radiation to be transmitted through the top cover plate, wherein a portion of the top cover plate includes an epitaxial Si film constructed from at least one of Si-on-Sapphire and Si-on-Quartz, patterning and depositing a gold film on the epitaxial Si film to create a Si—Au eutectic perimeter fence, at least one interconnect, at least one contact pad and at least one mounting pad for securing and interconnecting at least one internal component located within the device cavity, the at least one internal component including at least one of a photovoltaic cell and a photodetector, wherein the bottom substrate is constructed of a high resistivity Si substrate material, wherein the bottom substrate includes a signal processing device and a light emitting diode serving as an optical transmitter, wherein the bottom substrate includes bonding pads and interconnects deposited on a patterned insulating layer of grown or deposited oxide, wherein the bottom substrate has a plurality of partial Si vias (PSV) for electrically connecting at least one of the internal components with at least one device located on an outer surface of the bottom substrate, wherein the plurality of partial Si vias (PSVs) are electrically isolated from each other and are formed by introducing a dopant having an opposite conductivity to that of the high resistivity Si substrate, wherein the bottom substrate hosts a plurality of bottom substrate pads and the cover plate host a plurality of cover plate pads, wherein the bottom substrate pads and the cover plate pads are aligned with each other and include gold bumps of varying height to permit connectivity between components located on the cover plate and the signal processing device and the light emitting diode, wherein the Si side of the cover plate, top and bottom surfaces of the at least one Si spacer and a top side of the bottom substrate are deposited with a continuous gold fence on an outer perimeter, wherein one side of the gold fence is bonded to a Si surface forming a gold-Si eutectic mixture and wherein an opposing side of the gold fence is bonded to a like gold fence using a gold-to-gold bond to seal the device platform, A miniaturized device platform is provided and includes a first substrate and a second substrate configured to form an enclosure, the second substrate being constructed from a high-resistivity semiconductor material, wherein the miniaturized device platform is immersed in a corrosive and high temperature external environment, the enclosure housing a plurality of internal components and being configured to isolate the plurality of components from the external environment, the miniaturized device platform configured to allow reception and transmission of electromagnetic radiation through at least one of the first substrate and the second substrate, wherein the enclosure includes a plurality of partial-semiconductor-vias (PSVs) configured to electrically connect at least one of the plurality of internal components with an external component, wherein the partial-semiconductor-vias (PSemVs) are constructed on a thinned section of the second substrate and are created by introducing an impurity to the second substrate, the combination of the second substrate and the impurity configured to provide electrical conductivity, wherein the first substrate and the second substrate are cohesively sealed using a combination of at least one of an epitaxial interface, a eutectic mixture, a metal silicide, and a metal to metal bond.

DETAILED DESCRIPTION OF THE INVENTION

Figure 1:
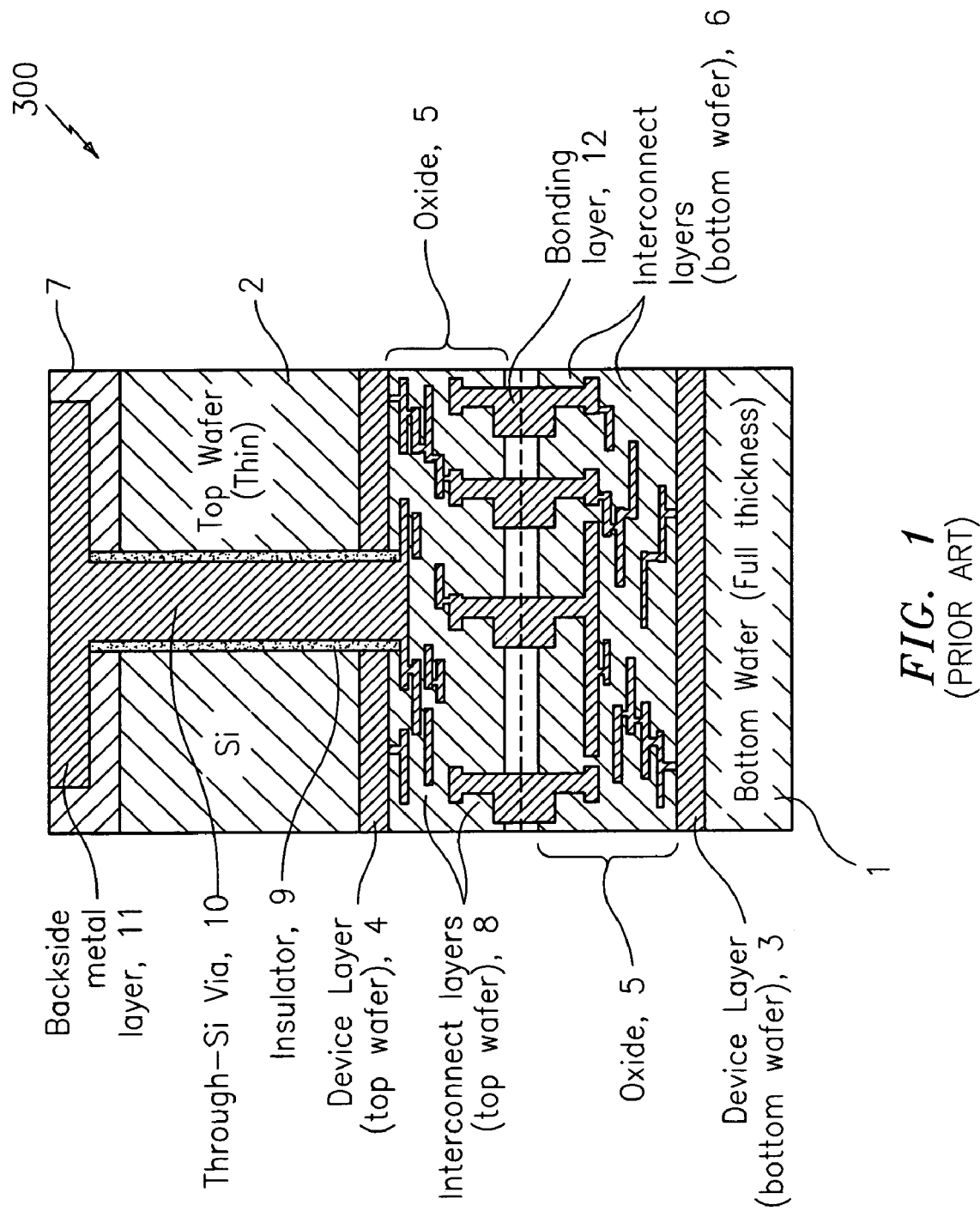
FIG. 1 is a cross-sectional view of an integrated circuit (IC) illustrating the device packaging in accordance with the prior art, where the IC includes a variety of interconnects via through-Si-via (TSV) and flip-chip bonding of two individual IC wafers.

In accordance with an exemplary embodiment of the present invention, a miniaturized, implantable, biosensor platform along with a methodology for implementing the miniaturized, implantable biosensor platform is provided. It should be appreciated that the biosensor platform may include at least one electrochemical biosensor that may be exposed to body fluids, as well as one or more sub-components that need to be hermetically sealed. Accordingly, depending on the application it is contemplated that some components and/or sub-components of the platform may need to be sealed, while other components and/or sub-components may need to be exposed. For example, when configured for use as a glucose monitor, the sensing elements need to be exposed, while the processing devices should be sealed. It is contemplated that these sub-components may come in individual sub-chips that may include electronic and opto-electronic devices as well as integrated circuits (ICs). One or more of these sub-components may interface with the electrochemical biosensors and may be configured to process their signals by converting them into a form that can be wirelessly transmitted via optical, ultrasound and/or radio frequency (RF) waves to an external unit. In addition, a variety of powering devices may be included with these sub-components and may include, but are not limited to, photovoltaic (PV) solar cells, RF receivers, biofuel cells, etc.

In accordance with an exemplary embodiment, the biosensor may contain a multiplicity of two-terminal and/or three-terminal electrochemical sensors configured to detect glucose and/or other metabolite sensors (such as Lactate, oxygen, carbon dioxide, dopamine, glutamate, etc.). However, it should be appreciated that only one electrochemical sensor may be used if desired. Additionally, programmable potentiostat circuitry as well as various signal processing circuitry (such as analog-to-digital circuitry (ADC)) may be also included, where the programmable potentiostat circuitry may be used to drive the electrochemical sensors and may be configured to interface with the various signal processing circuitry. It is contemplated that the various signal processing circuitry may be integrated with existing devices or they may be provided in a separate IC chip. Additionally, the powering source for this miniaturized implantable biosensor may be based on PV solar cells, which may be integrated with existing IC's or which may be realized via a separate IC chip. This separate IC chip may also include one or more photodetectors to receive external commands in the form of optical radiation of various and different wavelengths, wherein the wavelengths may or may not be adjustable as desired. Wireless communication may be realized using a light emitting diode (LED) or laser that is interfaced with the signal processing chip. It should be appreciated that although a light emitting diode (LED) or laser is disclosed herein with regards to realizing the wireless communication, any RF frequency suitable to the desired end purpose may be used.

Moreover, due to the corrosive nature of body fluids, these sub-chips should be hermetically packaged within a miniaturized enclosure (which may also be sealed), which is in operable electrical communication with the subcutaneous, body-fluid-immersed electrochemical sensing element. In accordance with the invention, such packaging methodology provides for a biosensor platform that is robust enough to exclude oxygen and body fluids from its internal cavity for extended periods of time (i.e. few months to few years). Moreover, the invention provides for a biosensor platform that may be extremely miniaturized so that it fits within the bore of a small diameter needle to minimize tissue damage when being inserted into a body.

Figure 2:
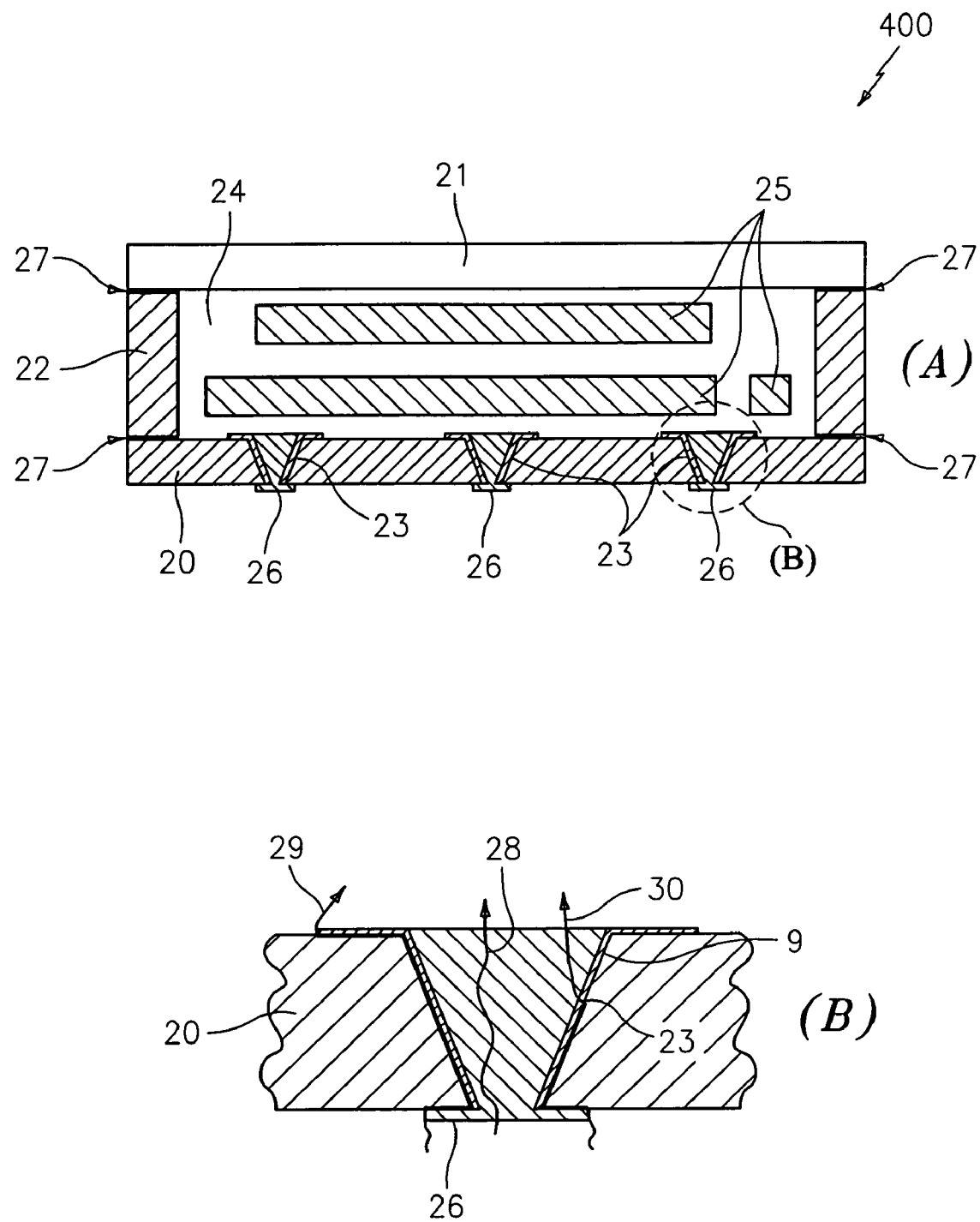
FIG. 2 is a cross-sectional view of a typical sub-chip enclosure in accordance with the prior art where the electrical interconnects have been achieved using through-Si-vias (TSVs).

Referring to FIG. 2, a cross-sectional schematic of a typical enclosure 400 in accordance with the prior art is illustrated where various components (25) of a sensor platform are housed within a sealed cavity (24), wherein the enclosure 200 includes at least one sensor terminal (26) (shown herein as having three (3) sensor terminals (26)). The cavity (24) of the enclosure 200 may be created by sandwiching at least one spacer (22) between a transparent top cover (21) and a bottom wafer (20) with a seal (27) between the spacers (22) and the transparent top cover (21) and the bottom wafer (20). The electrical connection from the inside of the enclosure 200 to the three sensor terminals (26) may be accomplished via three through-Si-vias (TSVs) (23) where the space between the TSVs (23) and the bottom wafer (20) are sealed. However, using current sealing techniques, the seals (27) and TSVs (23) of enclosure 200 are typically prone to leakage in harsh environments, such as during prolonged exposure to body fluids. The exploded view B of the TSVs (23) and sensor terminal (26) shown in FIG. 2 illustrates three possible leakage pathways associated with the TSVs (23), i.e. pin-hole leakage (28), as well as interface delamination (29) involving the sensor terminal (26) and/or the TSV isolation (9) along with pin-hole leakage (30) from the TSV isolation (9).

In accordance with the present invention, packaging having the desired body-fluid resistance characteristics may be accomplished by integrating some or all of the following features into the enclosure 400 of FIG. 2. Referring to FIG. 3, an enclosure 500 which integrates the features discussed hereinafter is illustrated in accordance with one embodiment of the present invention, where the features may include, i) eliminating delaminating interfaces, ii) increasing interfacial adhesion, and/or iii) eliminating through-Si-vias (TSVs) interconnects at the bottom side of the enclosure. Regarding the elimination of delaminating interfaces, prolonged exposure of layered structures to moisture and/or corrosive liquids typically results in delamination. One approach to resolve this issue involves using epitaxially grown layers (32) between two structures where little or no strain or interfacial voids can be found between the two structures. For example, interfaces between epitaxially grown Si on sapphire (SOS) and Si on quartz are of high integrity. This allows transparent top cover (21) to be integrated with a Si film, where the Si film can have its native $SiO_2$ removed from its exposed face (for example, using an HF treatment) to yield a $SiO_2$-free Si film (31).

Regarding the increase of interfacial adhesion, typically prolonged exposure of metal-semiconductor and metal-insulator interfaces to moisture and/or corrosive liquids are also prone to delamination. However, annealing evaporated Au films (33) on $SiO_2$-free Si film (31) and/or Si substrates (22) and (20) above about 363° C. in a reducing atmosphere (about 5% forming gas) followed by a gradual cooling to room temperature, forms a Au—Si eutectic mixture (34) having superior adhesion qualities. Such alloy provides a natural transition between the Si substrate and the gold deposit that is used later on to hermetically seal the structure using Au—Au seals (37), which may be attained by thermo-compression and/or thermo-sonic bonding techniques. In one embodiment, it is contemplated that the spacer (22) may have a plurality (such as two) Au/Si eutectic perimeter seals which may be mirrored on the top cover (21) and bottom substrate (20). In still another embodiment, the spacer (22) can be replaced by a gold preform or patterned foil.

Lastly, regarding the elimination of through-Si-vias (TSVs) interconnects at the bottom side of the enclosure 500, TSVs are susceptible to delamination, as well as the presence of micro-cracks and pinholes through the supporting substrate (i.e. the bottom substrate (20)). In order to achieve electrical interconnects across the bottom substrate, partial-silicon-vias (PSVs) (36) may be formed by the selective diffusion of a dopant impurity at a specified location. Since dopant diffusion requires long times to take place over a thick substrate, a partial etching (35) may be performed to make it practical. Typically, n-type impurities are diffused across a high resistivity p⁻ Si wafer, using patterned $SiO_2$ mask. The resultant n-type diffused region is surrounded by p⁻-type Si, which results in a natural electrical isolation between adjacent PSV interconnects. It should be appreciated that similar results may be obtained with diffusing p-type impurities on n-type high resistivity substrates. In an alternative embodiment, ion implanting of n-type impurities in p-substrate and subsequent thermal annealing to remove the lattice damage may also be used to achieve the desired PSVs. In another embodiment, PSV can be formed in a number of semiconductor substrates other than Si. These are termed as partial-semiconductor-vias (PSemVs). For example, semiconductor substrates like Ge, ZnSe, ZnS, SiC, etc. can be used for the formation of PSemVs.

Figure 3A:
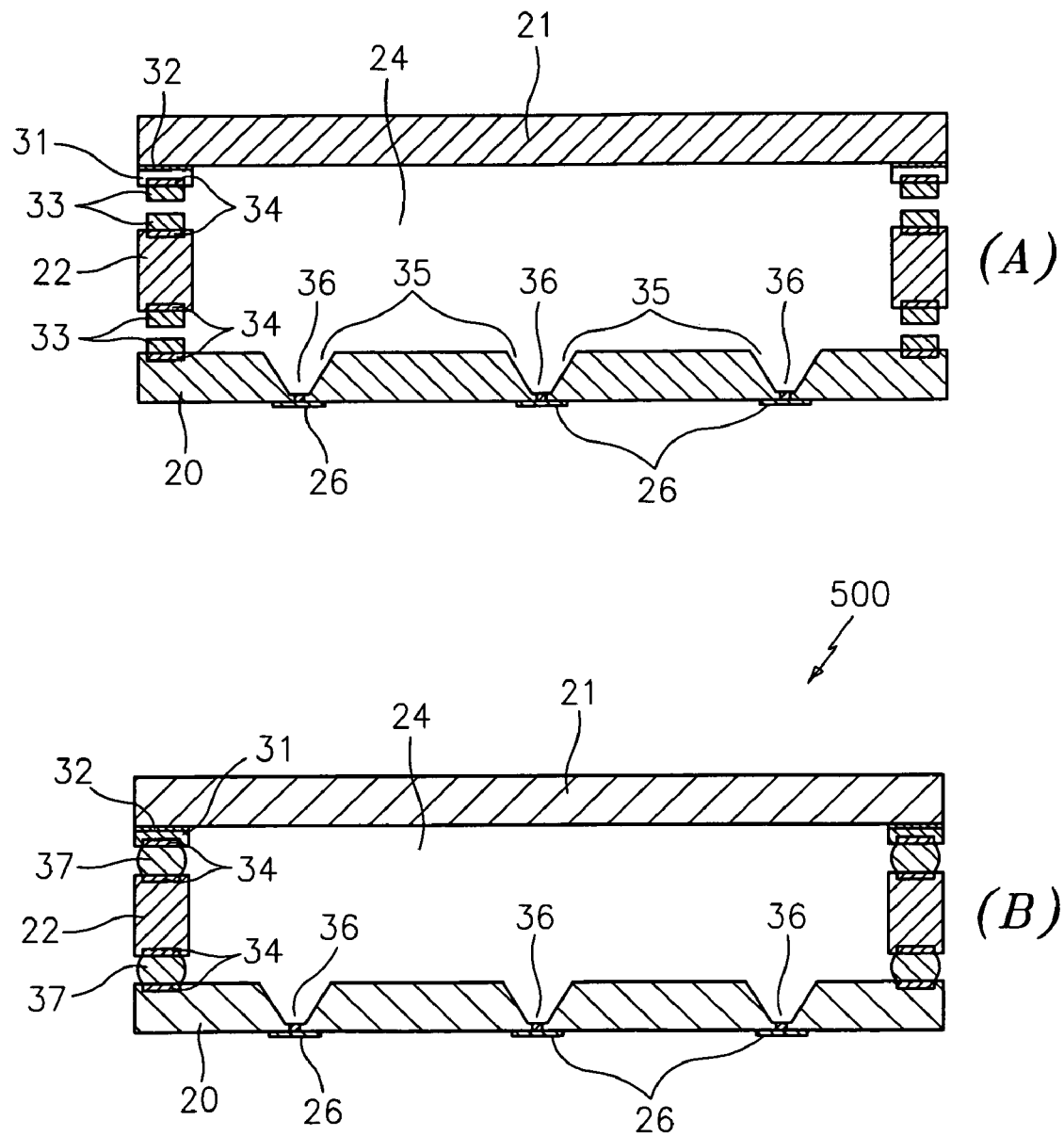
FIG. 3A is a schematic block diagram of a hermetically sealed enclosure incorporating partial-Si-vias (PSVs) along with epitaxial Si-on-insulator cover, Au/Si eutectic interfaces and Au—Au seals in accordance with the present invention.
Figure 3B:
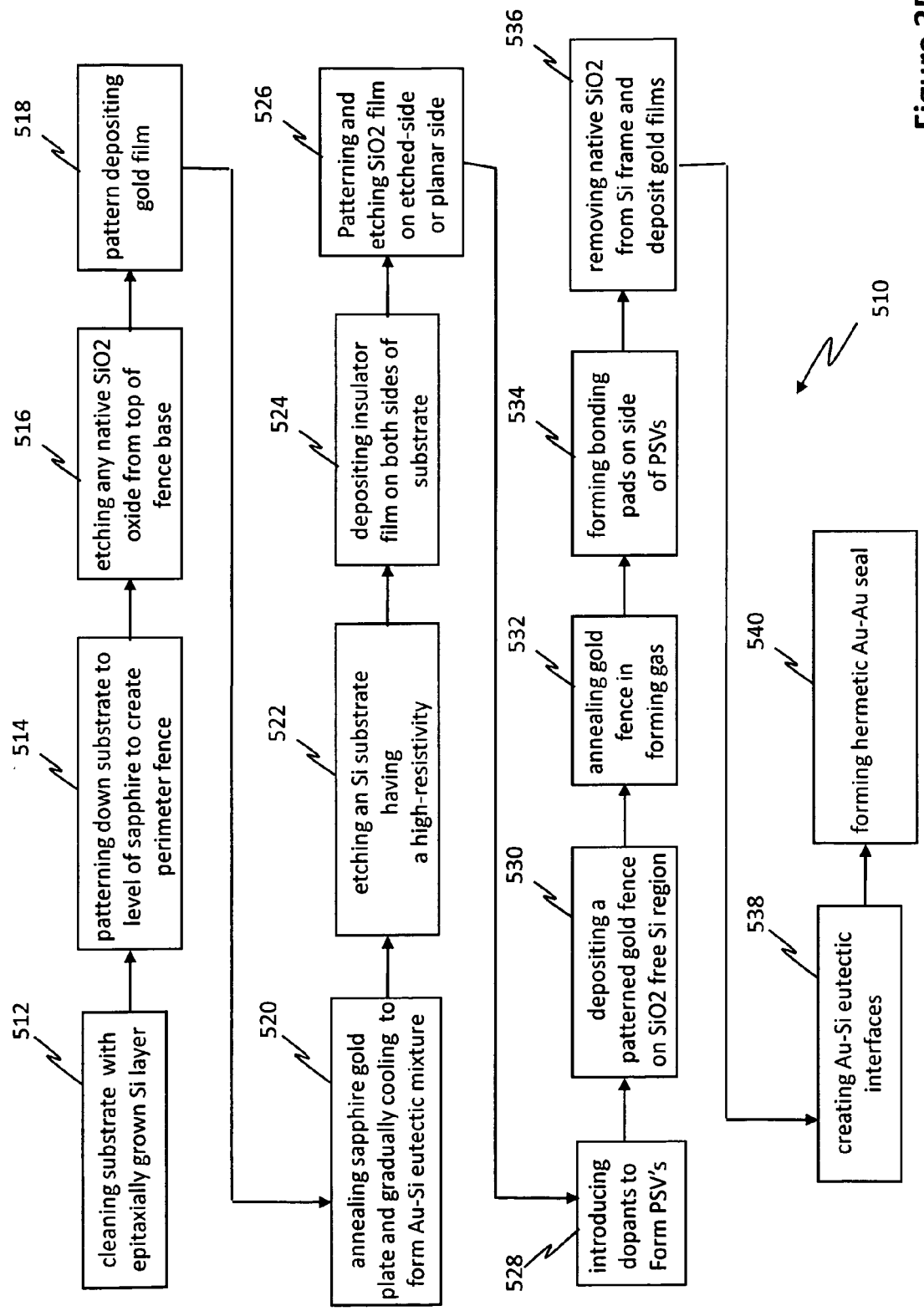
FIG. 3B is a block diagram illustrating a method for creating the enclosure of FIG. 3A.

Referring to FIG. 3B, a block diagram illustrating a method 510 for creating the enclosure 500 of FIG. 3A is provided in accordance with the present invention. Regarding the cover plate, the method 510 includes cleaning a single crystal sapphire substrate (which can be used as transparent top cover (21)) with an epitaxially grown Si layer (31) having a thickness of about 0.01 microns to about 50 microns (and more specifically, of about 0.1 microns to about 1 micron and more optimally of about 0.3 microns to about 0.5 microns), and having a robust Si-sapphire interface (32), as shown in operational block 512. The cleaned single crystal sapphire substrate (21) is patterned down to the level of sapphire to create a Si perimeter fence base, as shown in operational block 514. The method 510 includes etching any native $SiO_2$ oxide from the top of the Si perimeter fence base, as shown in operational block 516, and pattern depositing a gold film of about 0.5 microns in thickness, as shown in operational block 518. The sapphire cover plate (21) is annealed at between about 375° C. to about 400° C. in a forming gas atmosphere (for example, about 5-15% $H_2$ with the balance of $N_2$) followed by a cooling to room temperature to form a Au—Si eutectic mixture (34) possessing superior adhesion quality at the Au—Si interface, as shown in operational block 520. It should be appreciated that, if desired the gold film may be built up with additional gold layers using a variety of deposition processes such as electrochemical or electroless plating, evaporation or sputtering of Au followed by patterning, screen or ink-jet printing of gold nanoparticles, etc. If additional layers are built up, then a heat treatment step may be required to consolidate the Au deposit and remove any organics.

Regarding the high resistivity Si substrate, the method 510 includes etching a Si substrate having a resistivity in the range of about 10,000 Ω·cm, (preferably about 30,000 Ω·cm and more preferably about 60,000 Ω·cm), with either p-type or n-type doping, from one side to create etched regions (35) leaving a thin section of Si with remaining thickness in the order of about 1 micron to about 100 microns (preferably about 5 microns to about 50 microns and more preferably about 20 microns to about 30 microns), as shown in operational block 522. The method 510 includes depositing an insulator film, such as thermally grown or physically deposited $SiO_2$, on both sides of the Si substrate (not shown in FIG. 3), as shown in operational block 524. The method 510 further includes patterning and etching the $SiO_2$ film in the etched-side or the planar side to open windows for the introduction of desired dopant impurities to form electrically conducting partial-Si-vias (PSVs), as shown in operational block 526, and introducing dopant impurities to form PSVs, as shown in operational block 528. It should be appreciated that the dopant impurities may be introduced using any method suitable to the desired end purpose. For example, one method of introducing the dopant impurities involves using a diffusion furnace operating at about 1,000° C. to create PSVs (36). The duration of this introduction is commensurate to the aforementioned thickness of the thin Si section. Another method for PSV formation involves ion implantation followed by a heat treatment to remove the lattice damage. In the case of ion implantation, the deposited dopant impurities could be driven to higher depths using a high temperature (about 1,000° C. to about 1,100° C.) treatment. It should be further appreciated that the type of dopant may be chosen to be of opposite conductivity to that of the high resistivity Si substrate. For example, n-type phosphorous impurity diffusion is performed for p-type high resistivity Si substrates. In the case of n-type high resistivity Si substrates, diffusion of boron p-type impurity is performed.

The method 510 includes depositing a patterned gold perimeter fence (33) onto an SiO2-free region, as shown in operational block 530, which may be created by buffered oxide etching on the covering oxide layer of the high resistivity Si substrate (20), and annealing the gold perimeter fence in forming gas (as discussed above) to form the Au—Si eutectic interface (34), as shown in operational block 532, where the gold layer (33) can be built up to a desired thickness as discussed hereinabove. The method 510 also includes forming bonding pads (26) on one or both sides of the PSVs (36) (here only the bonding pad (26) on the planar side of the high resistivity Si substrate is shown), as shown in operational block 534. This may be accomplished by depositing a patterned Au film onto $SiO_2$-free PSV region as well as the $SiO_2$-covered portions, the latter of which may permit formation of interconnects. It should be appreciated that similarly to the perimeter fence discussed hereinabove, an annealing step in forming gas may allow the formation of ohmic contact with the PSVs. In case of n-diffused PSV regions, the gold containing trace amounts of antimony or arsenic can be used to ensure low resistivity PSV contacts.

Regarding the Si frame (22), the Si frame (22) may be created via a variety of cutting and/or etching tools as desired, such as laser machining, deep-reactive ion etching, chemical etching, ion-beam milling, ultra-sonic grinding, etc. The method 510 also includes removing the native $SiO_2$ layer on the top and bottom surfaces of the Si frame (22) and depositing gold films (33) on both sides with patterns similar to those used for fence formation on the cover plate (50) and high resistivity Si substrate (20), as shown in operational block 536. The method 510 further includes creating the Au—Si eutectic interfaces (34) via a heat treatment in forming gas, as shown in operational block 538. The method also includes aligning and sandwiching the Si frame (22) between the cover plate (21) and high resistivity Si substrate (20) and subjecting the combination to thermocompression or thermosonic bonding to form a hermetic Au—Au seal, as shown in operational block 540. It should be appreciated that such a procedure can take place in a variety of combinations as desired. For example, the cover plate (21) may first be bonded with the Si frame (22), and the high resistivity Si substrate (20) may then be bonded afterwards or vice versa.

Figure 4:
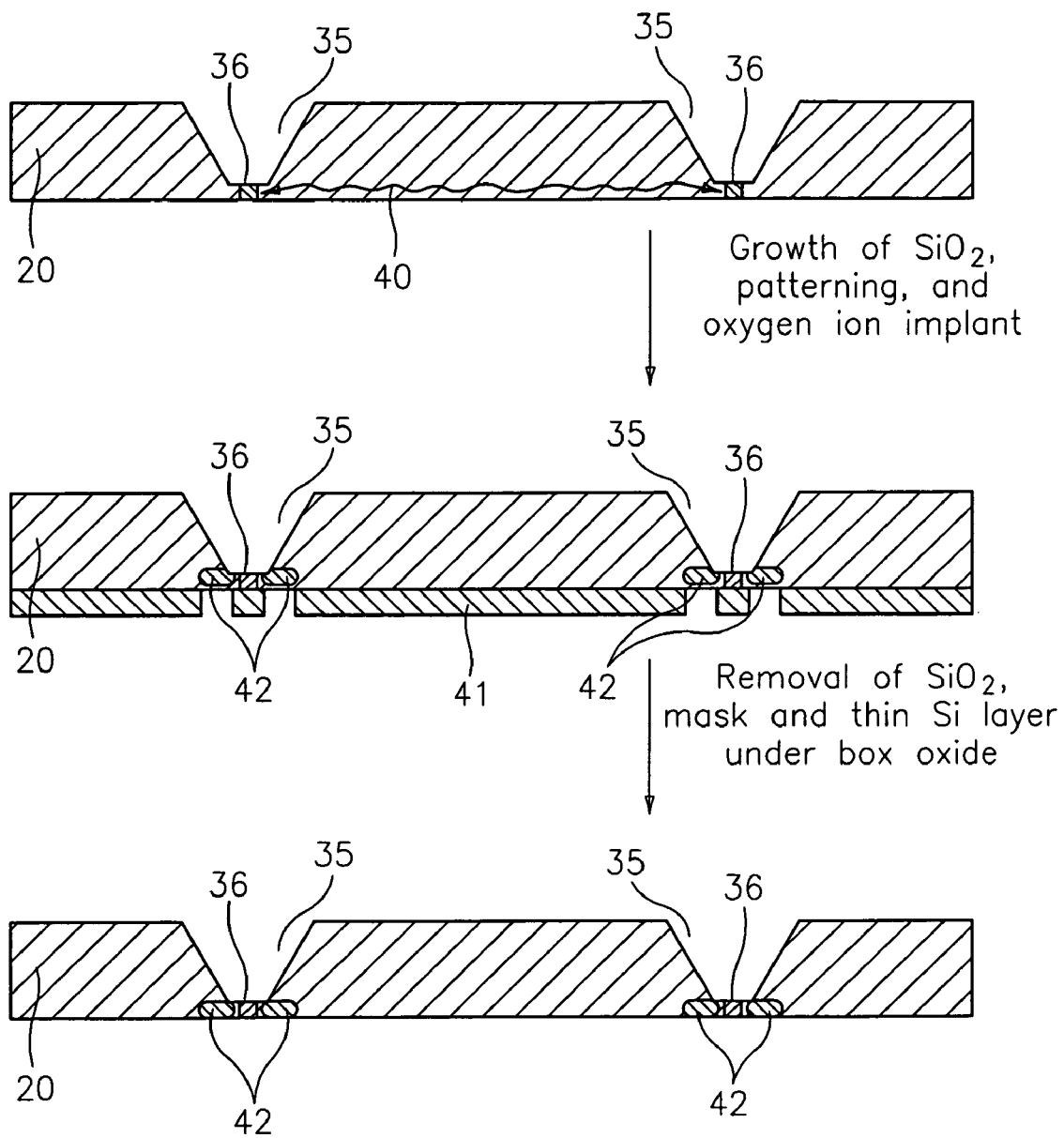
FIG. 4 is a schematic block diagram of the bottom wafer of the hermetically sealed enclosure of FIG. 3 showing the electrical isolation between adjacent partial-Si-vias (PSVs).

Referring to FIG. 4, one technique for achieving additional isolation characteristics (i.e. to eliminate possible electrical cross talk shown in (40)) between adjacent PSVs (36) is illustrated and includes using an appropriate mask (41), where oxygen implantation followed by annealing results in the formation of box oxide (42) around the PSVs (36). It should be appreciated that since the ion implantation typically penetrates over a couple of microns, the etched region (35) should have such a depth that it leaves Si regions of a few micron-thin (thick) for PSV diffusion.

Figure 5A:
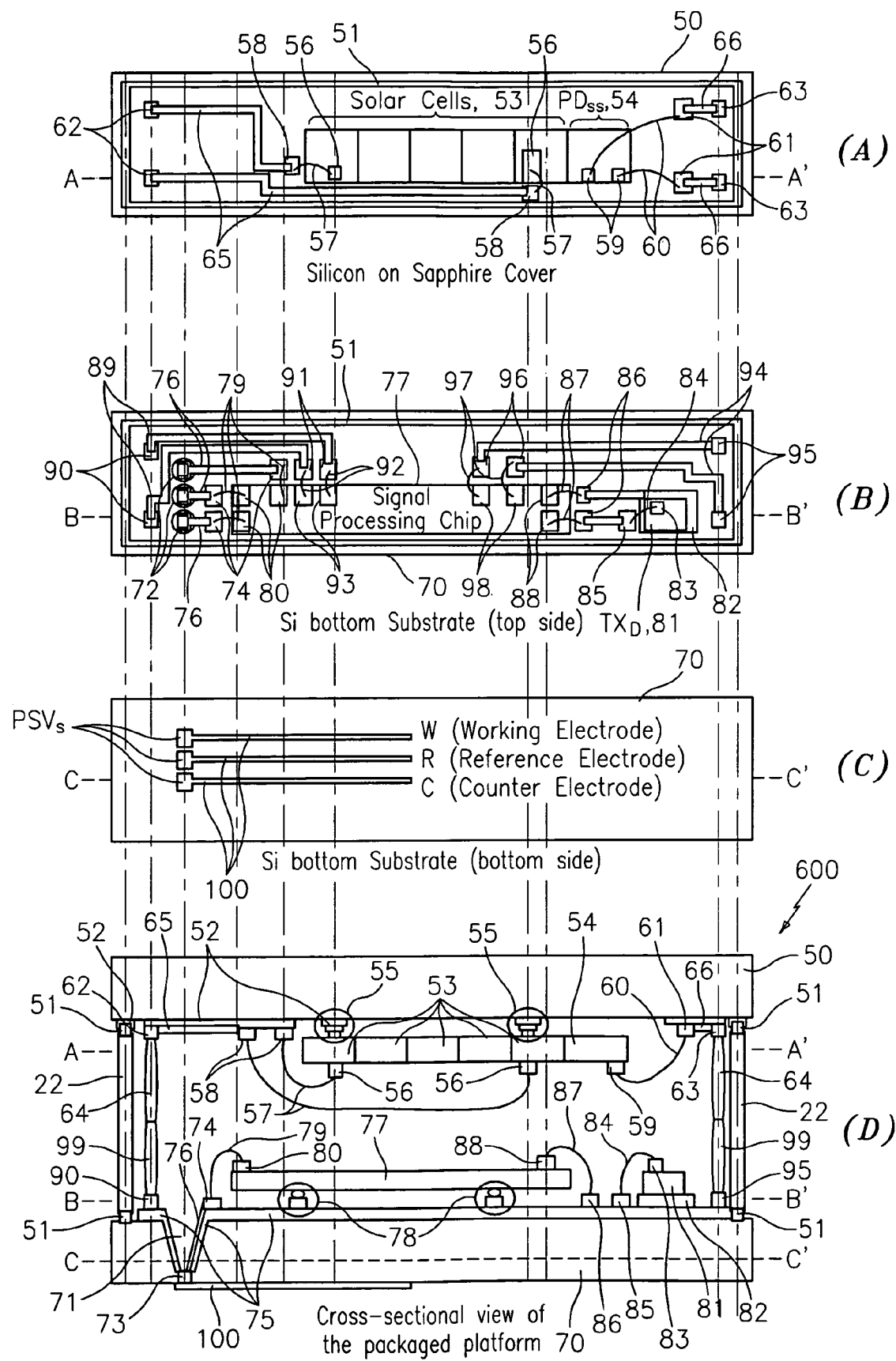
FIG. 5A is a schematic block diagram of a biosensor platform in accordance with one embodiment of the present invention illustrating the use of wire bonding to integrate various sub-chips within a hermetically sealed enclosure.

Referring to FIGS. 5(a)-(d), the topology of an integrated biosensor platform having an enclosure 600 and using patterned interconnects and wire bonds, in accordance with the invention is illustrated. As shown in FIG. 5a, the topology of cover plate (50) (i.e. transparent top cover 21) is illustrated and includes, immediately around the perimeter of the cover plate (50), a perimeter Au fence (51) realized on a patterned Si film (52) located directly underneath (shown in FIG. 5d). This patterned Si film (52) is part of (i.e. grown on epitaxially) the cover plate (50), which may be constructed from Si-on-sapphire (SOS). The cover plate (50) includes back-illuminated solar cells (53) and photodetector $PD_{ss}$ (54), which may be mounted onto the SOS cover plate (50). It should be appreciated that although these devices (i.e. back-illuminated solar cells (53) and photodetector $PD_{ss}$ (54)) may be secured to the cover plate (50) via gold pads (55) through a Si/Au/Si eutectic (shown in FIG. 5(d)), any method or materials suitable to the desired end purpose may be used to secure these devices to the cover plate (50). It is contemplated that Mo and Moly Silicide may be used in place of gold-Si eutectic. Moreover, since Mo to Moly bond is not as low temperature as gold-gold, an intermediate material that alloys with Moly may be used in place of gold. The pads (56) on solar cells (53) may be wire bonded (57) to pads (58) which may be formed on the patterned Si film (52) on the SOS cover plate (50). Similarly the pads (59) on the $PD_{ss}$ photodetector (54) may also be wire bonded (60) to pads (61) similarly formed on the patterned Si film (52) on the SOS cover plate (50). It should be appreciated that pads (58) and (61) may be interconnected to two outer left (62) and two outer right (63) pads (where gold bump (64) is formed (See FIG. 5d)), using interconnects (65) and (66), respectively. These interconnects (65) and (66) may be formed by patterning Au deposited on either the sapphire or the patterned Si film (52) of SOS cover plate (50).

Figure 5E:
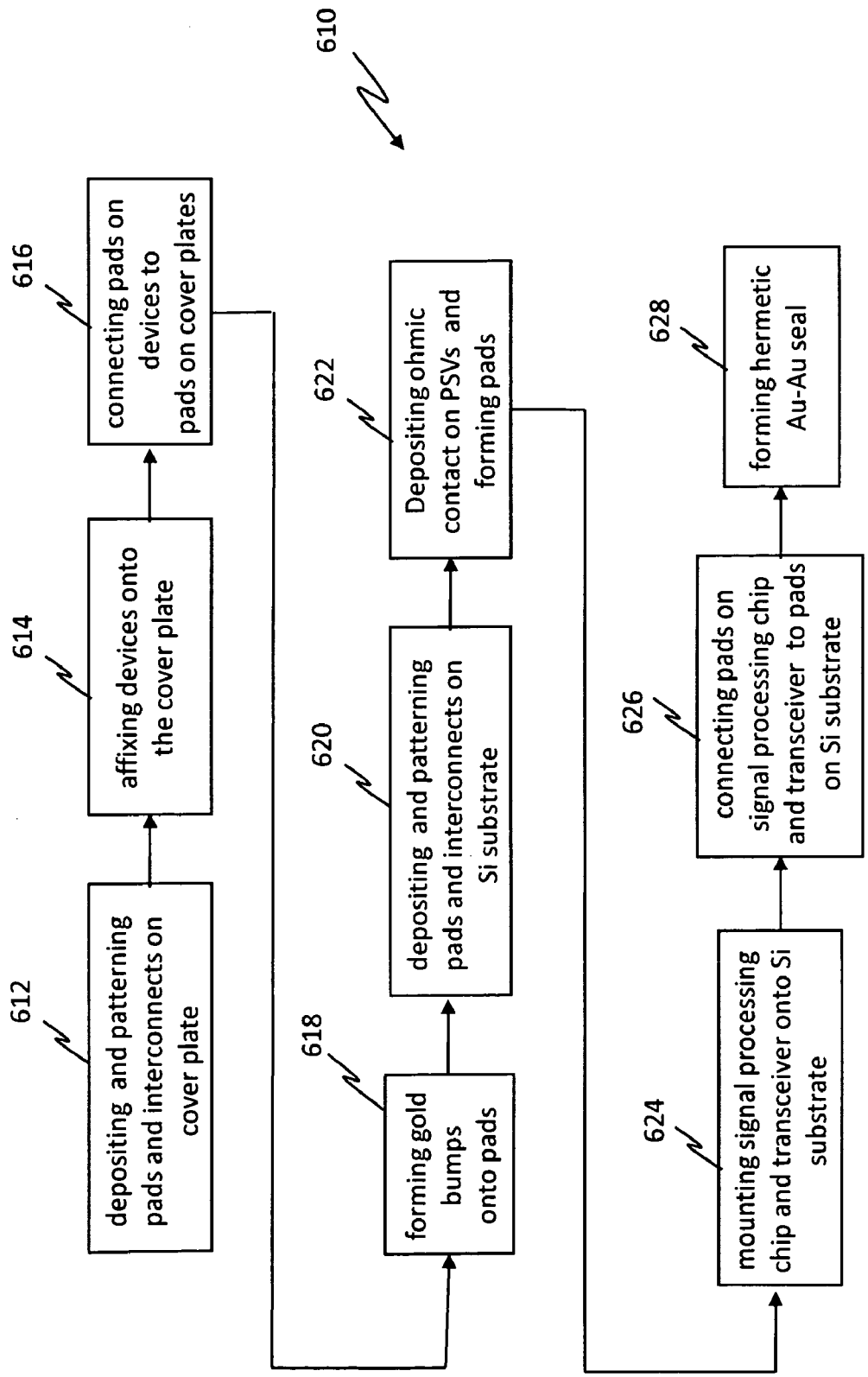
FIG. 5E is a schematic block diagram illustrating a method for creating the enclosure of FIGS. 5a-5d.

As shown in FIG. 5E, the topology of the high-resistivity bottom Si substrate (70) (i.e. bottom wafer 20) is illustrated in a similar fashion to SOS cover plate (50) and may also include a perimeter Au fence (51) immediately surrounding the perimeter of the bottom Si substrate (70). A region (71) may be etched (See FIG. 5(d)) to form at least one (in this case three) partial-Si-vias (PSVs) (72) in predetermined locations also as shown by a box (73) in FIG. 5d. As shown, three pads (74) (one for each PSV) may be formed and connected (76) with the top contact of its respective PSV. To avoid electrical crosstalk, the pads (74) as well as their interconnects (76) may be patterned on a $SiO_2$ layer (75) formed on the Si substrate (70) (shown in FIG. 5(d)). A signal processing chip (77) may be included and may be mounted onto the Si substrate (70) using Au pads (78) (shown in FIG. 5(d)). Subsequently, wire bonds (79) may be used to connect the sensor pads (74) to their equivalent pads (80) on the signal processing chip (77). In a similar fashion, the $TX_D$ LED or laser (81) may be affixed on its pad (82) and its top contact pad (83) may be wire bonded (84) to an adjacent pad (85), where the adjacent pad (85) together with pad (86) may be wire bonded (87) onto the respective pads (88) on the signal processing chip (77), where pad (86) is connected to $TX_D$ pad (82). Interconnects (89) may be configured to join the two outer left pads (90) with the pads (91), where outer pads (90) may be wire bonded (92) to the power and ground pads (93) of the signal processing chip (77). In a similar fashion, interconnects (94) may be configured to connect the two outer right pads (95) with the pads (96) which may wire bonded (97) to pads (98) on the signal processing chip (77). This affords the connection of the PDss photodetector (54), mounted on the cover plate (50) to the signal processor unit (77) located on the Si bottom substrate (70). It should be appreciated that pads (90) and (95) may be gold bumped (99) and thermo-compression bonded with the top cover bumps (64), along with the perimeter fence (51), as (shown in FIG. 5(d)). Referring to FIG. 5c, the topology of the high-resistivity bottom Si substrate (70) from the bottom side is illustrated and shows the respective PSVs (73), also shown in FIG. 5(d), that may be connected to three electrochemical electrodes (100) located on the bottom side of the high-resistivity bottom Si substrate (70).

Referring to FIG. 5E, a block diagram illustrating a method 610 for creating the enclosure 600 of FIG. 5(d) is provided in accordance with the present invention. Regarding the Si-on-sapphire cover plate (50), the method 610 includes depositing and patterning, on either pre-patterned Si regions on sapphire or Si-etched sapphire substrate or a combination of both (in FIG. 5(d) both pads and interconnects are shown to be formed onto pre-patterned Si regions), pads (62), (63), (58), (61) and (55) and interconnects (65) and (66), as shown in operational block 612. It should be appreciated that the pads (62), (63), (58), (61) and/or (55) and interconnects (65) and (66) can be made from a variety of metals (gold, aluminum, copper, etc.) and/or other conductive materials (i.e. graphene, nanotubes, heavily doped Si, conductive oxides, etc.). The method 610 further includes affixing devices (such as solar cells (53) and photodetector ($PD_{SS}$) (54)) onto the pads (55) on the cover plate (50) using any method suitable to the desired end purpose (such as flip-chip thermocompression or thermosonic bonding), as shown in operational block 614. The method 610 further includes connecting the pads on the devices (i.e. solar cells (53) and $PD_{ss}$ (54)) to the corresponding pads on the cover plate (50), as discussed above and as shown in operational block 616. It is contemplated that this may be accomplished via any method suitable as desired, such as by wire bonding. The method 610 also includes forming gold bumps (64) onto pads (62) and (63), as shown in operational block 618.

Regarding the high resistivity Si substrate (70) as shown in FIGS. 5(b)-5(d), the method 610 includes depositing and patterning pads (90), (95), (74), (91), (96), (86), (85), (82) and (78) and interconnects (65), (89) (94) and (76) onto $SiO_2$ covered substrate, as shown in operational block 620. The method 610 further includes depositing the ohmic contact (such as may be formed by gold silicon eutectic) on PSVs (73) from the etched side (71) and forming pads (72), as shown in operational block 622. It should be appreciated that this may be accomplished in accordance with the process defined hereinabove with regards to the fabrication of pads (26) in FIG. 3 and that for certain applications, pads may be formed on oxide layer deposited on silicon high resistivity substrate or directly on the substrate without any oxide underneath. The method also includes mounting the signal processing chip (77) onto pads (78) and $TX_D$ onto pad (82), as shown in operational block 624, using any method suitable to the desired end purpose, such as flip-chip bonding or other techniques. At this point, the method 610 may include connecting (using wire bonding or other acceptable method) the pads on the signal processing chip (80), (93), (98) and (88) (shown in FIG. 5(b)) and $TX_D$ (83) devices to corresponding pads on the Si substrate, as described hereinabove and as shown in operational block 626, and forming gold bumps (99) having a desired height, onto pads (90) and (95).

Regarding the Si spacer frame (22), the Si frame (22) may be created as discussed hereinabove with regards to enclosure 500 in FIG. 3. It should be appreciated that as discussed hereinabove the Si spacer (22) may be replaced by a gold preform of similar dimensions. Accordingly, the method 610 includes includes aligning and sandwiching the Si frame (22) between the cover plate (50) and high resistivity Si substrate (20) and subjecting the combination to thermocompression or thermosonic bonding to form a hermetic Au—Au seal, as shown in operational block 628. It should be appreciated that such a procedure can take place in a variety of combinations as desired. For example, the cover plate (50) may first be bonded with spacer (22), and the high resistivity Si substrate (20) may be bonded afterwards or vice versa. Here it should be noted that such thermocompression or thermosonic bonding procedures not only seal the perimeter fence but also allows Au—Au bonding between bumps (64) and (99) and may necessitate that the bump height be carefully controlled to afford internal electrical interconnection within the enclosure.

Figure 6:
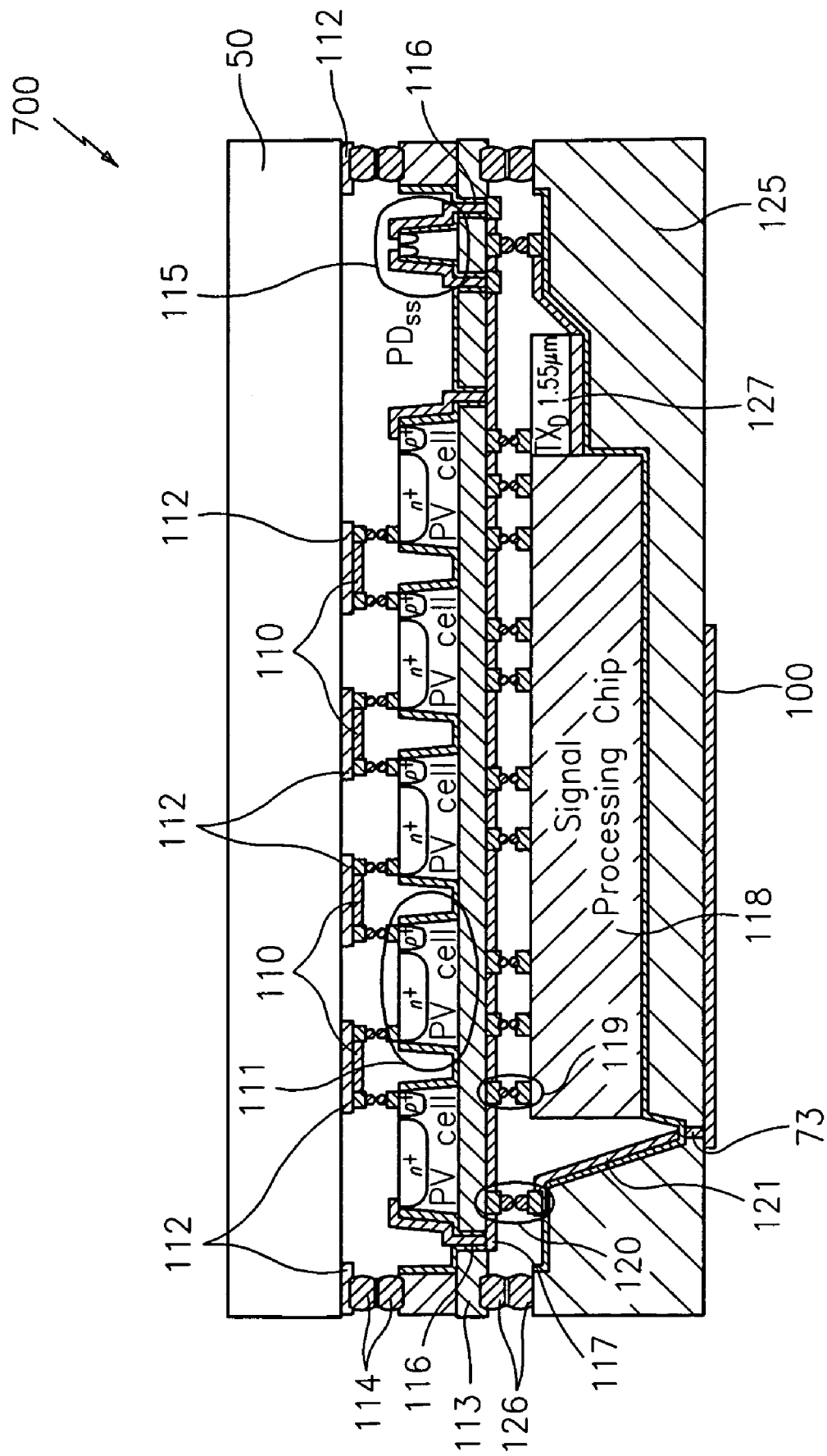
FIG. 6 is a schematic block diagram of a biosensor platform in accordance with one embodiment of the present invention using flip-chip bonding to integrate various sub-chips within a hermetically sealed enclosure.
Figure 7:
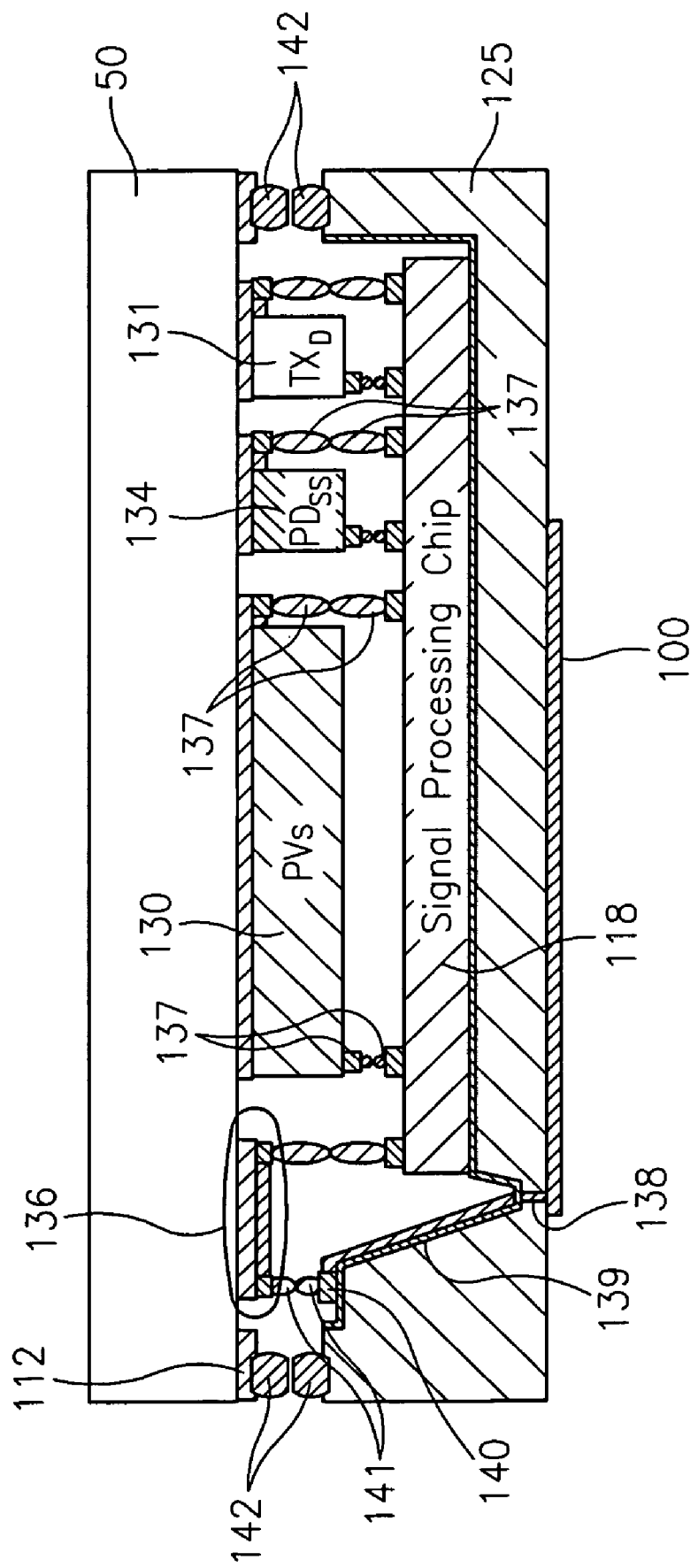
FIG. 7 is a schematic block diagram of a biosensor platform in accordance with one embodiment of the present invention using an alternate flip-chip bonding procedure to integrate various sub-chips within a hermetically sealed enclosure.

Referring to FIGS. 6 and 7, two alternate embodiments for implementing the packaged functional devices discussed herein are provided, wherein the packaged functional devices do not use wire bonding. FIG. 6 illustrates a three-layered structure, where the top SOS cover (50) may be used to provide interconnects (110) onto the various solar cells (111) of the solar array located within sealed cavity (104) and (105) of enclosure 700. The interconnects (110) may be formed on patterned Si (112) of the SOS structure (50) and the solar cells (111) may be front illuminated and front contacted and realized on a high resistivity substrate (113). The $PD_{SS}$ photodetector (115) may be of similar architecture and may also be formed on substrate (113). Thermo-compression bonding of SOS structure (50) and high resistivity substrate (113) may provide both solar cell interconnection as well as perimeter fence (114). It should be appreciated that solar and/or photodetector $PD_{SS}$ output may be provided through either PSVs or TSVs (here TSVs are shown (116) for explanation) to a distributed interconnect (117) located at the bottom side of high resistivity substrate (113). The distributed interconnect (117) may be used to direct power and $PD_{SS}$ signal to a signal processing unit (118) through any number of Au pads and bumps (119). This distributed interconnect (117) may also be used to connect the $TX_D$ LED or laser (127) that may be located on an appropriately recessed additional high resistivity substrate (125). Similarly, the distributed interconnect (117) may also be used to connect the biosensor(s) (100) to the PSVs (73) via the Au bumps and pads (120) and patterned interconnect (121). Similarly as above, thermo-compression bonding between the high resistivity substrates (113) and (125) may also provide connections for both electrical interconnection as well as acting to seal a second perimeter fence (126).

FIG. 7 illustrates a packaging structure 800 where the PV cell(s) (130), the $TX_D$ LED or laser (131), and/or the $PD_{SS}$ photodetector (134) are flip-chip mounted onto the SOS top cover plate (50). Subsequently, the appropriate height bumps (137) may be achieved using the respective contacts of the PVs (130), $TX_D$ LED or laser (131), $PD_{SS}$ photodetector (134), SOS interconnect (136) and/or the signal processing unit (118) to afford flip-chip bump-to-bump bonding and component interconnection. The composite assembly of SOS top cover plate (50) and/or signal processing unit (118) may be connected and sealed to an appropriately recessed high resistivity Si substrate (125) which contains PSVs (138), their interconnects (139), bonding pads (140), appropriate height bumps (141) and a Au/Si eutectic perimeter fence (142). In this embodiment, the height of the gold bumps (137) and (141) should be controlled to obtain an internally interconnected and sealed package platform. It should be appreciated that the gold bumps (137) or studs may be of variable heights and they connect pads which are also located at different heights. Also, the gold fence (51) formation and the gold bump interconnect realization typically occur at the same time. Accordingly, the gold bumps (137) should be fairly accurate with respect to the gold fence (51).

In an additional embodiment, the SOS top cover (50) may serve as a substrate to monolithically grow PVs (130), $TX_D$ LED or laser (131), $PD_{SS}$ photodetector (134), and/or other devices such as signal processing (118) devices. In this case, any or all of the above devices can be interconnected using a distributed interconnect placed in the high resistivity substrate (125) in the place where the signal processing chip is shown in FIG. 7 (or elsewhere as desired). This essentially involves flip-chip bonding of two wafers. In the case of the signal processing chip (118) being a separate unit, the integration may resemble that of FIG. 7. In still yet another embodiment, the top cover (50) may be constructed from a wide energy gap semiconductor material, such as GaP, ZnSe, ZnS, SiC, ZnO, etc. It should be appreciated that the band gap may be relative to the powering source (solar cells) which typically operate in the visible range (1.8 eV for 0.7 micron red light). For example, one acceptable band gap range may be between 1.8 eV-3.7 eV. These semiconductor materials can be used in place of the sapphire cover and can be epitaxially coated with a thin layer of Si to protect their outer surface from exposure to body fluids. Alternatively, a germanium (Ge) film can be used in place of Si, which also forms eutectic alloys with gold. Still yet another embodiment involves the formation of the signal processing chip (118), partial-Si-Vias (138), pads (140), interconnects (139), and/or perimeter fence (142) onto a high resistivity substrate (125), where the high resistivity substrate (125) is flip-chip bonded to the cover plate (50) and hosts all (or some) of the optical and/or optoelectronic devices.

Figure 8:
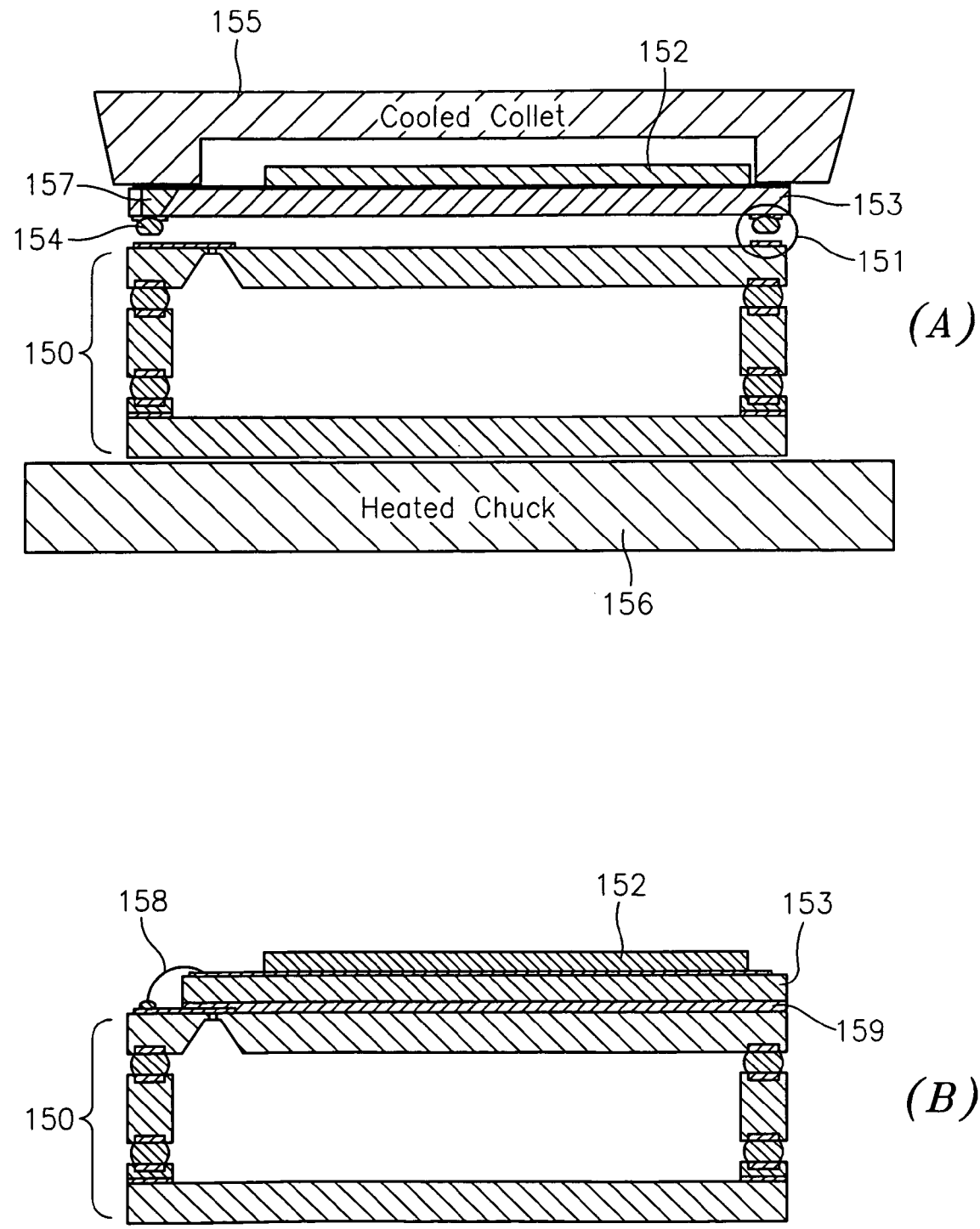
FIG. 8 is a schematic block diagram illustrating the bonding and interconnecting of a prefabricated, biosensor-containing wafer onto the integrated and hermetically sealed enclosure.

In accordance with the present invention, subsequent to packaging the electronic and optical components of the miniaturized implantable platform, appropriate coatings needed for biological detection should be deposited onto the proper components, where the coatings may typically contain a variety of proteins and hydrogels, which are temperature sensitive. Referring to FIG. 8, an embodiment where the bottom side of the packaged platform (150) is interfaced with a prefabricated biosensor (152) onto a substrate (153) is illustrated. One way to accomplish this configuration using the prefabricated biosensor (152) may involve flip-chip bonding using a cold chuck/collet (155) on the top of the package, and a heated chuck on the bottom (156) of the package (shown in FIG. 8A). It should be appreciated that the temperature range of the cold collet (155) may be about −80° C. to about 95° C. and more preferably about −40° C. to about 55° C. However, an exemplary temperature range may be about 3° C. to about 37° C. For this configuration thermo-sonic bonding may be used together with gold bumped (154) TSVs (157), where another set of dummy gold bumped pads (151) may be placed on the opposing side of the packaged platform (150) between the platform (150) and the substrate (153) of the prefabricated biosensor (152) to provide both planarity and additional adhesion. Alternatively, an ultra-sonic wire bonding (158) approach may be used together with a polymeric adhesive (159).

Figure 9:
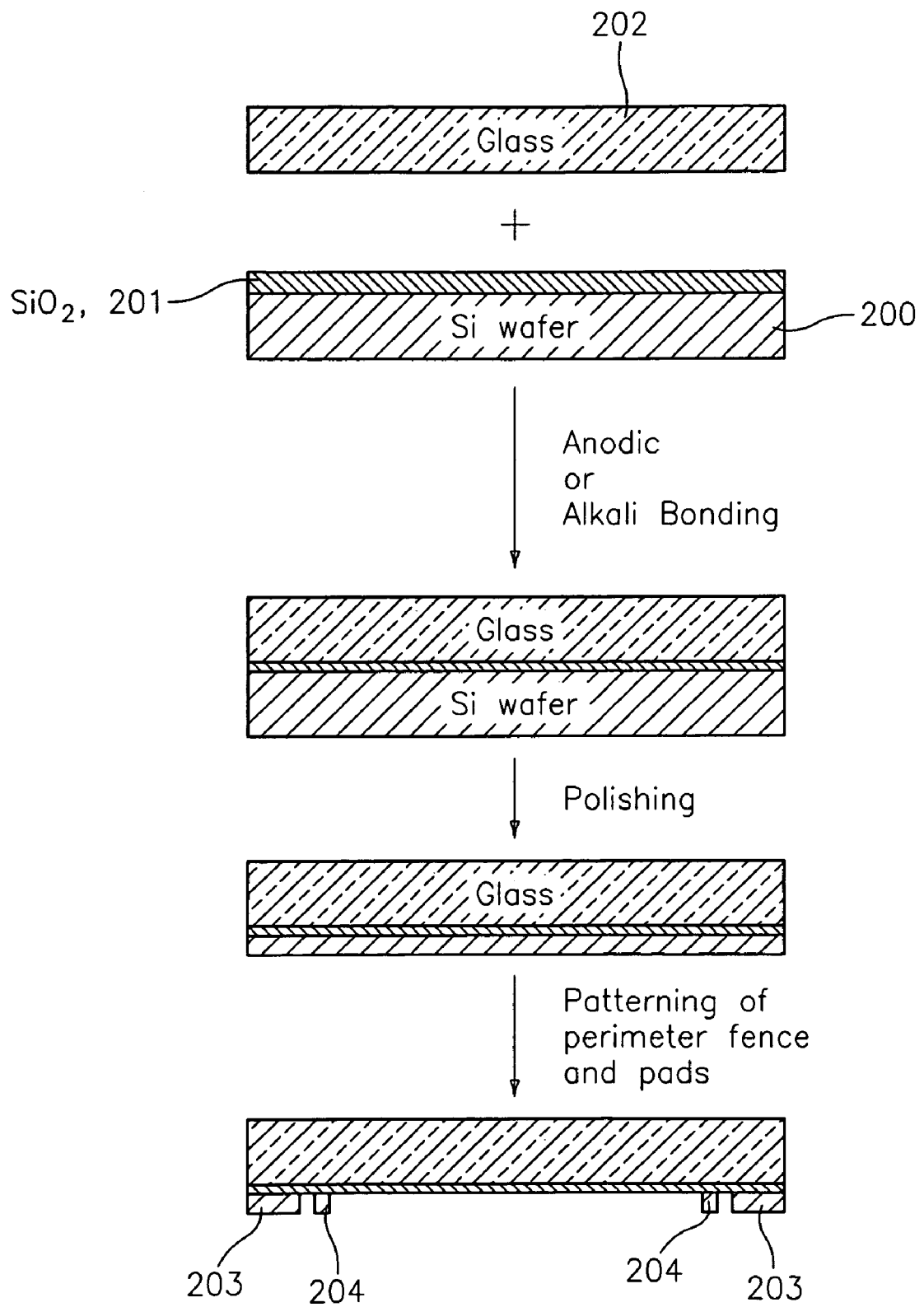
FIG. 9 is a schematic block diagram illustrating an alternative methodology to attain transparent glass covers with patterned Si films.

Referring to FIG. 9, an alternative to using epitaxial Si-on-sapphire or Si on quartz cover plates (50) is illustrated and includes using alkali or anodic bonding of a Si wafer (200), where its native oxide (201) may be bonded to a glass substrate (202). Subsequently, following wafer thinning (from the silicon side), Si patterning may permit the formation of pads (204) and a high integrity gold fence (203) as described hereinabove and as shown in FIG. 3.

In another embodiment, the cover plate may be made of quartz and a thin film of patterned molybdenum (Mo) may be deposited where the perimeter seal is needed. Typically, Mo/quartz seals are known to withstand high temperature and vacuum conditions. This Mo film may then be covered with a thin film of Si, which may be physically deposited using sputtering or some other appropriate deposition method(s) as desired. Upon heat treatment, Mo forms MoSi, which provides superior adhesion between Si and Mo. As such, any remaining Si can be used to form an Si/Au eutectic substance, which can subsequently be used to form Au—Au seals. In still yet another embodiment, the top cover plate can be achieved using a polycrystalline Si film on substrates like glass, quartz, AlN, SiC, sapphire, ZnS, ZnO, etc. It is contemplated that various types of materials may be used to increase the operation temperature envelop of the platform to very high temperatures. These materials may include Molybdenum (Mo), Pt, Pd, Ni, etc, all of which form silicides which form a good bond like Au—Si eutectic.

It it contemplated that the article, implementation and/or fabrication of the invention may be embodied in forms that can be used for other applications than those disclosed herein. For example, various computing hardware and IC chips can be packaged within such miniaturized enclosures and directly attached onto devices that operate in a vacuum, under water, in corrosive liquids and gases, and other biological media. One such application may involve actuation of artificial muscles or various other microelectromechanical devices. The enclosure described herein can easily be adapted to house miniaturized pressure transducers at the site where PSVs are formed. Here, a thin Si film can serve as a diaphragm. In one embodiment, a traditional variable capacitor pressure transducer, a strain gauge type resistor, or a transistor element can be implemented from the inside part of this enclosure and be protected from the corrosive environment. Similarly, a chem-FET device can be implemented on the exposed site and be interconnected with the passivated electronics through PSVs. Such devices, used in conjunction with remote powering and remote sensing can find a number of applications for nanosized robots together with diagnostic devices, smart dust sensors and satellite- or drone-operated distributed network of sensors.

Another application may include nanosized batteries in proximity to biological and other environments that cannot tolerate any leakage of battery electrolytes. Such nanosized packages incorporate battery electrolytes as well as cathodes and anodes within the enclosure, with the PSVs serving as the electrical contacts to the outside world (i.e. component external to the enclosure). Similarly, these or other PSVs can serve to charge these batteries by connecting them to biological fuel cells on the outside (i.e. external to the enclosure). In addition, these batteries can be remotely charged using photovoltaics cells, thermoelectric generators, RF powering sources etc. housed inside the enclosure.

Another application for such enclosures, particularly using high temperature materials such as MoSi, may involve situations that will expose the platform to high temperature environments, such as jet engines, automotive catalytic convertors, rockets, geothermal exploration, space crafts, nuclear environments, etc. Here, thermoelectric, photovoltaics and/or electromechanical sources can be also housed within the enclosure to protect them from the harmful effects of high temperatures and radiation. These devices can be used to power the devices within these enclosures. In still yet another application, PSV technology can be used to facilitate 3D integration of multiple IC chips. Here, the PSV technology is also complementary with liquid cooling using corrosive liquids like sea water.

In accordance with the present invention, the invention may be implemented as discussed in U.S. patent application Ser. No. 11/862,866 filed Sep. 27, 2007, the contents of which are incorporated herein in its entirety. For example, take the case of a glucose sensor. As disclosed in U.S. patent application Ser. No. 11/862,866, the integrated biosensor platform disclosed herein may be implanted subcutaneously in a subject such that the sensor elements sense characteristics of a body fluid of the subject. An external control unit located external to the body of the subject can communicate with the integrated biosensor platform via electromagnetic signals (such as via solar cells and/or photodetector ($PD_{SS}$)) to transmit and receive signals to and from the integrated biosensor platform.

The implementation and/or fabrication of the invention may be embodied in the form of a computer or controller implemented processes, in whole or in part. The invention may also be embodied in the form of computer program code containing instructions embodied in tangible media, such as floppy diskettes, CD-ROMs, hard drives, and/or any other computer-readable medium, wherein when the computer program code is loaded into and executed by a computer or controller, the computer or controller becomes an apparatus for practicing the invention. The invention can also be embodied in the form of computer program code, for example, whether stored in a storage medium, loaded into and/or executed by a computer or controller, or transmitted over some transmission medium, such as over electrical wiring or cabling, through fiber optics, or via electromagnetic radiation, wherein when the computer program code is loaded into and executed by a computer or a controller, the computer or controller becomes an apparatus for practicing the invention. When implemented on a general-purpose microprocessor the computer program code segments may configure the microprocessor to create specific logic circuits.

While the invention has been described with reference to an exemplary embodiment, it will be understood by those skilled in the art that various changes, omissions and/or additions may be made and equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

We claim:

1. A device platform, which contains at least one internal component, wherein the device platform is configured to isolate the at least one internal component from an environment external to the device platform while providing for electrical connectivity to at least one external component externally located on the outer surface of the said device platform, the device comprising:
    an enclosure, said enclosure including a top cover plate and a bottom substrate configured to define a sealed enclosure cavity for containing the at least one component,
    wherein said top cover plate is configured to allow reception and transmission of electromagnetic radiation, the surface of said top cover plate adjacent said enclosure cavity being covered with an epitaxial Si film in intimate cohesion, and
    wherein said bottom substrate is constructed of a high resistivity Si having a Si substrate material conductivity and includes at least one partial Si via (PSV), wherein said at least one partial Si via (PSV) is configured to electrically connect said at least one internal component with said at least one external component, and
    wherein said partial Si via (PSV) is formed by introducing a dopant with said Si material, wherein the combination of said dopant and said Si material results in at least one of a reduced conductivity and a conductivity that is opposite to that of said Si substrate material conductivity, and
    wherein an outer perimeter of each of said surface of said top cover plate adjacent said enclosure cavity and a surface of said bottom substrate adjacent said enclosure cavity includes a continuous gold fence cohesively bonded to its respective Si surface, wherein said top cover plate and said bottom substrate are configured such that said enclosure cavity is sealed using a gold-to-gold bond.

2. The device of claim 1, wherein said at least one internal component includes a plurality of components, and wherein said at least one external component includes a plurality of components, and wherein said at least one partial Si via (PSV) includes a plurality of partial Si vias (PSVs), each of said plurality of partial Si vias (PSVs) being electrically isolated from each other and electrically connected to one of said plurality of internal and external components.

3. The device of claim 2, wherein said external component is a biosensor.

4. The device of claim 3, wherein the said biosensor is selected from electrochemical biosensor and chemical field effect transistors (Chem-FETs).

5. The device of claim 1, wherein said device is miniaturized to fit inside of a hypodermic needle.

6. The device of claim 1, wherein said top cover plate is constructed from at least one of an epitaxial Si film on sapphire material, an epitaxial Si film-on-quartz material, an epitaxial Ge film-on-ZnSe material, an epitaxial Si film on ZnS material and an epitaxial Si film on SiC material.

7. The device of claim 1, wherein said at least one partial Si via (PSV) is formed by at least one of,
- diffusing n-type dopants into a p-type substrate having a high resistivity,
- implanting n-type dopants into a p-type substrate and performing thermal annealing to remove lattice damage,
- diffusing p-type dopants into an n-type substrate having a high resistivity,
- implanting n-type dopants into a p-type substrate and performing thermal annealing to remove lattice damage, and
- diffusing p-type dopants into a p-Si substrate having a high resistivity, and isolating said diffused regions by surrounding them with ion implanted box oxide.

8. The device of claim 1, wherein said partial Si vias (PSVs) are isolated from each other by surrounding them with ion implanted box oxide.

9. The device of claim 1, wherein said at least one internal component includes at least one photodetector and at least one photovoltaic cell contained within said enclosure cavity such that electromagnetic energy transmitted through at least one predetermined region of said top cover plate is incident upon said at least one photodetector and at least one photovoltaic cell, wherein said epitaxial Si film may be removed to enhance radiation transmission through said predetermined regions.

10. The device of claim 9, wherein said at least one component further includes a signal processing device, wherein said signal processing device is connected with said at least one photovoltaic cell using at least two photovoltaic cell interconnects and wherein said signal processing device is connected with said at least one photodetector using at least two photodetector interconnects, wherein said photovoltaic cell interconnects and said photodetector interconnects are created by patterning said epitaxial Si film on said surface of said top cover plate within said enclosure cavity, where said photovoltaic cell interconnects and said photodetector interconnects are constructed from a material having low electrical resistivity.

11. The device of claim 10, wherein said at least one photovoltaic cell interconnect and said at least one photodetector interconnect are constructed from at least one of gold, silver, aluminum, palladium, platinum and copper.

12. The device of claim 1, wherein said enclosure further includes at least one Si spacer located between said top cover plate and said bottom substrate to define a sealed enclosure cavity for containing the at least one component, wherein the outer perimeter of said at least one spacer also includes a continuous gold fence bonded cohesively to its respective Si surface and wherein when said at least one Si spacer, said top cover plate and said bottom substrate form said enclosure cavity, said continuous gold fence on said top cover plate is gold-to-gold bonded to said continuous gold fence on said top surface of said at least one spacer and said continuous gold fence on said bottom substrate is bonded to said continuous gold fence on said bottom surface of said at least one spacer to seal said enclosure cavity.

13. The device of claim 12 where the said spacer is a patterned gold perform with similar dimensions as the gold fence.

14. The device of claim 1 wherein said cohesive bonding is achieved by the formation Au—Si eutectic.

15. The device of claim 1, wherein cohesively bonding between Si and gold is achieved by the formation of a silicide.

16. The device of claim 15, wherein said silicide includes at least one of Molybdenum, Palladium, Platinum, Titanium, and Nickel.

17. The device of claim 1, wherein said top cover plate includes a polycrystalline Si film on a substrate which includes at least one of glass, quartz, AlN, SiC, sapphire, ZnS ZnSe, and ZnO.

18. The device of claim 1, wherein said top cover plate is constructed from a glass substrate and a Si wafer, where said glass substrate is bonded to said Si wafer, wherein said Si wafer is thinned.

19. A method for integrating a plurality of device into a device platform, wherein the device platform contains at least one internal component and is configured to isolate the at least one internal component from an environment external to the device platform while providing for electrical connectivity to at least one external component externally located on the outer surface of the device platform, and wherein the device includes an enclosure, the enclosure including a top cover plate and a bottom substrate configured to define a sealed enclosure cavity for containing the at least one component, wherein the top cover plate is configured to allow reception and transmission of electromagnetic radiation, the surface of the top cover plate adjacent the enclosure cavity being covered with an epitaxial Si film in intimate cohesion, and wherein the bottom substrate is constructed of a high resistivity Si having a Si substrate material conductivity and includes at least one partial Si via (PSV), wherein the at least one partial Si via PSV is configured to electrically connect the at least one internal component with the at least one external component, and wherein the partial Si via (PSV) is formed by introducing a dopant with the Si material, wherein the combination of the dopant and the Si material results in at least one of a reduced conductivity and a conductivity that is opposite to that of the Si substrate material conductivity, and wherein an outer perimeter of each of the surface of the top cover plate adjacent the enclosure cavity and a surface of the bottom substrate adjacent the enclosure cavity includes a continuous gold fence cohesively bonded to its respective Si surface, wherein the top cover plate and the bottom substrate are configured such that the enclosure cavity is sealed using a gold-to-gold bond, the method comprising:
- forming the device platform using a top cover plate and a bottom substrate separated by at least one Si spacer, wherein said device platform defines a device cavity and said top cover plate is configured to allow electromagnetic radiation to be transmitted through said top cover plate, wherein a portion of said top cover plate includes an epitaxial Si film constructed from at least one of Si-on-Sapphire and Si-on-Quartz;
- patterning and depositing a gold film on said epitaxial Si film to create a Si—Au eutectic perimeter fence, at least one interconnect, at least one contact pad and at least one mounting pad for securing and interconnecting at least one internal component located within said device cavity, said at least one internal component including at least one of a photovoltaic cell and a photodetector, wherein said bottom substrate is constructed of a high resistivity Si substrate material,
- wherein said bottom substrate includes a signal processing device and a light emitting diode serving as an optical transmitter, wherein said bottom substrate includes bonding pads and interconnects deposited on a patterned insulating layer of grown or deposited oxide,
- wherein said bottom substrate has a plurality of partial Si vias (PSV) for electrically connecting at least one of said internal components with at least one device located on an outer surface of the bottom substrate,
- wherein said plurality of partial Si vias (PSVs) are electrically isolated from each other and are formed by introducing a dopant having an opposite conductivity to that of said high resistivity Si substrate, wherein said bottom substrate hosts a plurality of bottom substrate pads and said cover plate host a plurality of cover plate pads, wherein said bottom substrate pads and said cover plate pads are aligned with each other and include gold bumps of varying height to permit connectivity between components located on the cover plate and said signal processing device and said light emitting diode, wherein the Si side of said cover plate, top and bottom surfaces of said at least one Si spacer and a top side of said bottom substrate are deposited with a continuous gold fence on an outer perimeter, wherein one side of said gold fence is bonded to a Si surface forming a gold-Si eutectic mixture and wherein an opposing side of said gold fence is bonded to a like gold fence using a gold-to-gold bond to seal said device platform.

20. The method of claim 19, wherein said gold-to-gold bonding between said gold fences also enable the formation of respective gold bump to gold bump bonding to provide electrical connectivity between said components located on said cover plate and said components located on the bottom substrate.

21. The method of claim 19, wherein the said device platform is sealed such as to protect internal component from long-term exposure to moisture, oxygen, body fluids and corrosive environments.

22. The method of claim 19, wherein the said device located on an outer surface is comprised of a list of a biosensor, chemical sensor, nuclear radiation detecting sensor, temperature sensor, and pressure sensor.

23. The method of claim 19, where the said gold-to-gold bonding is performed using flip-chip thermocompression and thermosonic bonding techniques.

24. The method of claim 19, where at least one interconnect is realized by a wire bond.

25. The method of claim 19, wherein said top cover plate is constructed from at least one of an epitaxial Si film on sapphire material, an epitaxial Si film-on-quartz material, an epitaxial Ge film-on-ZnSe material, an epitaxial Si film on ZnS material and an epitaxial Si film on SiC material.

26. The method of claim 19, wherein said partial Si vias (PSVs) are formed in said high resistivity bottom substrate using at least one of,
diffusing n-type dopants into a p-type substrate having a high resistivity,
implanting n-type dopants into a p-type substrate and performing thermal annealing to remove lattice damage,
diffusing p-type dopants into an n-type substrate having a high resistivity, and
implanting n-type dopants into a p-type substrate and performing thermal annealing to remove lattice damage, and
diffusing p-type dopants into a p-Si substrate having a high resistivity, and isolating said diffused regions by surrounding them with ion implanted box oxide.

27. The method of claim 19, wherein said spacer is cohesively bonded with said top cover plate and said bottom Si substrate using a silicide.

28. The method of claim 27, wherein said silicide includes at least one of Palladium, Platinum Titanium, and Nickel.

29. The method of claim 19, wherein said gold bumps on said plurality of pads are constructed from at least of indium, indium alloys, tin and silver, and wherein said gold bumps are of varying height to permit connectivity between said partial-Si-vias (PSVs), said at least one component and said signal processing device.

30. The method of claim 19, wherein the said photovoltaic cells, photodetectors, and light emitting devices are monolithically grown on the said epitaxial Si film on the top cover plate.

31. The method of claim 19, wherein the said signal processing device is monolithically grown on the said high resistivity Si bottom substrate.

32. The method of claim 19, wherein the said spacer is another high resistivity substrate, said spacer substrate has a perimeter fence on either sides, said spacer substrate contains partial-Si-vias, through-Si-vias (TSVs), etched holes, electronic and optoelectronic internal components, interconnects pads, wire bonds and mounting pads for securing various internal components.

33. A miniaturized device platform, the miniaturized device platform comprising:
a first substrate and a second substrate configured to form an enclosure, said second substrate being constructed from a high-resistivity semiconductor material, wherein the miniaturized device platform is immersed in a corrosive and high temperature external environment, said enclosure housing a plurality of internal components and being configured to isolate said plurality of components from said external environment, said miniaturized device platform configured to allow reception and transmission of electromagnetic radiation through at least one of said first substrate and said second substrate, wherein said enclosure includes a plurality of partial-semiconductor-vias (PSVs) configured to electrically connect at least one of said plurality of internal components with an external component, wherein said partial-semiconductor-vias (PSemVs) are constructed on a thinned section of said second substrate and are created by introducing an impurity to said second substrate, the combination of said second substrate and said impurity configured to provide electrical conductivity, wherein said first substrate and said second substrate are cohesively sealed using a combination of at least one of an epitaxial interface, a eutectic mixture, a metal silicide, and a metal to metal bond.

34. The miniaturized device platform of claim 33, wherein said plurality of internal components includes at least one of an electronic device, an optoelectronic device, an integrated circuit device, a battery, micromechanical device, an ultrasound device, and a thermoelectric device.

35. The miniaturized device platform of claim 33, wherein said outside components are comprised of a list of a biosensor, chemical sensor, nuclear radiation detecting sensor, temperature sensor, and pressure sensor.

36. The miniaturized device platform of claim 33, wherein said outside components are comprised of a list of a power generating devices selected of a list of biofuel cell, fuel cell, battery, thermoelectric generator, micro-electromechanical energy generators.

37. The miniaturized device platform of claim 33, wherein the said reception and transmission of electromagnetic radiation through one of its substrates establishes at least one wireless link with a central control unit.

38. The miniaturized device platform of claim 37, wherein said at least one wireless link includes repeated wireless links with multiple miniaturized device platforms to collectively establish a network of miniaturized device platforms, said network of miniaturized device platforms providing environmental information at different locations.

* * * * *